US012569115B2

(12) United States Patent
Yamada

(10) Patent No.: US 12,569,115 B2
(45) Date of Patent: Mar. 10, 2026

(54) ENDOSCOPE SYSTEM, IMAGE GENERATION METHOD, AND STORAGE MEDIUM

(71) Applicant: OLYMPUS MEDICAL SYSTEMS CORP., Tokyo (JP)

(72) Inventor: Junya Yamada, Kawasaki (JP)

(73) Assignee: Olympus Medical Systems Corp., Tokyo (JP)

( * ) Notice: Subject to any disclaimer, the term of this patent is extended or adjusted under 35 U.S.C. 154(b) by 57 days.

(21) Appl. No.: 18/212,232

(22) Filed: Jun. 21, 2023

(65) Prior Publication Data

US 2023/0414065 A1 Dec. 28, 2023

Related U.S. Application Data

(60) Provisional application No. 63/354,258, filed on Jun. 22, 2022.

(51) Int. Cl.
*A61B 1/00* (2006.01)
(52) U.S. Cl.
CPC .... *A61B 1/000095* (2022.02); *A61B 1/00006* (2013.01)
(58) Field of Classification Search
CPC ..................... A61B 1/000095; A61B 1/00006
See application file for complete search history.

(56) References Cited

U.S. PATENT DOCUMENTS

| | | | | |
|---|---|---|---|---|
| 6,638,212 B1 * | 10/2003 | Oshima | .................. | A61B 1/045 |
| | | | | 600/110 |
| 2003/0142753 A1 * | 7/2003 | Gunday | ................... | H04N 7/18 |
| | | | | 382/254 |
| 2004/0024290 A1 * | 2/2004 | Root | ....................... | A61B 1/121 |
| | | | | 600/178 |
| 2008/0074492 A1 * | 3/2008 | Iwasaki | ................ | A61B 1/0638 |
| | | | | 600/109 |
| 2009/0234183 A1 * | 9/2009 | Abe | ................... | A61B 1/00165 |
| | | | | 356/73.1 |
| 2011/0037876 A1 * | 2/2011 | Talbert | ............... | A61B 1/00055 |
| | | | | 348/222.1 |
| 2018/0196250 A1 * | 7/2018 | Shimamoto | ............ | G02B 23/26 |
| 2020/0297433 A1 * | 9/2020 | Meagher | ................... | G06T 7/90 |
| 2020/0359875 A1 * | 11/2020 | Yamasaki | ........... | H04N 23/555 |
| 2022/0188988 A1 * | 6/2022 | Fukazawa | .............. | H04N 23/60 |

FOREIGN PATENT DOCUMENTS

| | | |
|---|---|---|
| JP | 08-022272 B2 | 3/1996 |
| JP | 2005-124823 A | 5/2005 |
| JP | 2008-149125 A | 7/2008 |
| JP | 2010-000185 A | 1/2010 |
| JP | 2013-502185 A | 1/2013 |
| JP | 2013-150666 A | 8/2013 |
| JP | 2016-005554 A | 1/2016 |

* cited by examiner

*Primary Examiner* — Zhubing Ren
(74) *Attorney, Agent, or Firm* — Morgan, Lewis & Bockius LLP

(57) ABSTRACT

An endoscope system includes a first processor and a second processor. The first processor is configured to receive an information including a number of times an endoscope is used, and determine if the number of times the endoscope is used is equal to or larger than a predetermined number of times. The second processor is configured to overwrite a first image correction data with a second image correction data when the first processor determines the number of times the endoscope is used is equal to or larger than the predetermined number of times.

20 Claims, 11 Drawing Sheets

ENDOSCOPE SYSTEM, IMAGE GENERATION METHOD, AND STORAGE MEDIUM

RELATED APPLICATION DATA

This application is based on and claims priority under 35 U.S.C. § 119 to U.S. Provisional Application No. 63/354, 258 filed on Jun. 22, 2022, the entire contents of which are incorporated herein by reference.

FIELD OF THE DISCLOSURE

The present disclosure relates to an endoscope system that corrects endoscopic image data using image correction data stored in an endoscope, an image generation method, and a storage medium.

BACKGROUND

Conventionally, endoscope systems that include an endoscope and a video processor have been introduced commercially. The video processor is configured to be connectable, for example, with a plurality of models of endoscopes. Depending on the model, endoscopes may vary in unique configurations such as pixel count of an image pickup device or length of an insertion portion.

For example, if there is a difference in pixel count, positions of OB (optical black) pixels and the like in a pixel column that are read out in raster scan order will vary as well. A difference in pixel count will also cause the video processor to perform different pixel count conversions according to display monitors. Furthermore, a difference in the length of the insertion portion will result in a difference in timing to read an image pickup signal from an image pickup device. In this way, processes performed by the video processor vary with the model of the endoscope.

Thus, generally, an endoscope is provided with a memory configured to store image correction data unique to the endoscope.

For example, Japanese Patent Application Laid-Open Publication No. 2013-502185 discloses a single-use image pickup device which includes a memory containing data that indicates features of the image pickup device. The image pickup device is used during a surgical operation to visualize a surgical area and is, for example, an endoscope.

SUMMARY OF THE DISCLOSURE

An endoscope system according to one aspect of the present disclosure includes a first processor and a second processor. The first processor is configured to receive an information including a number of times an endoscope is used, and determine if the number of times the endoscope is used is equal to or larger than a predetermined number of times. The second processor is configured to overwrite a first image correction data with a second image correction data when the first processor determines the number of times the endoscope is used is equal to or larger than the predetermined number of times.

An image generation method according to another aspect of the disclosure includes receiving information including a number of times an endoscope is used, and determining if the number of times the endoscope is used is equal to or larger than a predetermined number of times. When the number of times the endoscope is used is equal to or larger than the predetermined number of times, the method further comprises overwriting a first image correction data with a second image correction data.

A non-transitory computer-readable medium having instructions stored thereon, which when implemented by a processor causes the processor to execute a method, the method according to another aspect of the disclosure includes receiving information including a number of times an endoscope is used, and comparing the number of times the endoscope is used to a predetermined number of times. When comparing determines the number of times the endoscope is used is equal to or larger than the predetermined number of times, overwriting a first image correction data with a second image correction data, where the second image correction data is different from the first image correction data.

BRIEF DESCRIPTION OF THE DRAWINGS

FIG. 2 is a block diagram showing an electrical configuration of the endoscope system according to the first embodiment.

FIG. 9 is a block diagram showing an electrical configuration of an endoscope system according to a second embodiment.

FIG. 14 is a block diagram showing an electrical configuration of an endoscope system according to a third embodiment of the present disclosure.

DETAILED DESCRIPTION

Figure 1:
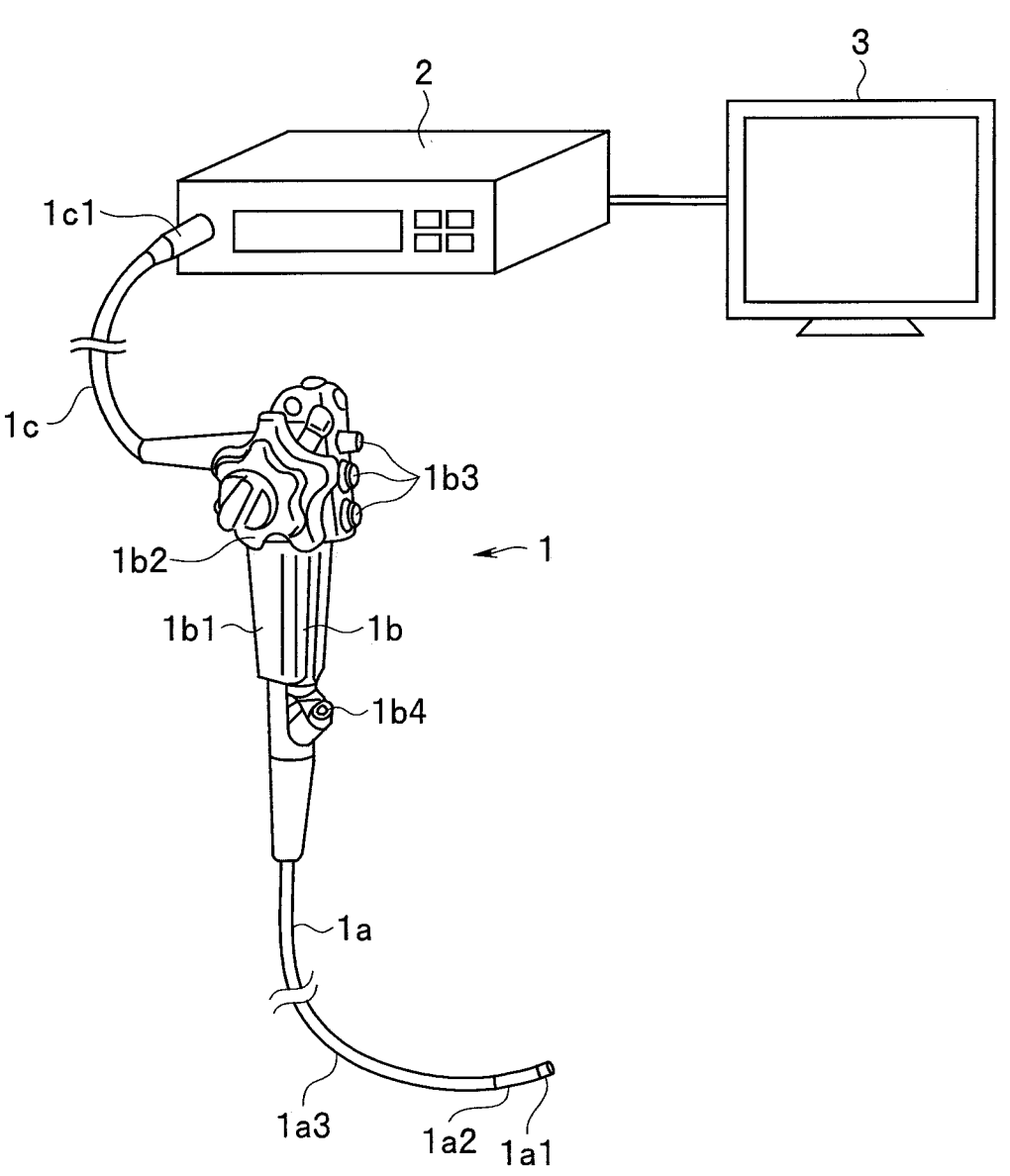
FIG. 1 is a perspective view showing a configuration of an endoscope system according to a first embodiment of the present disclosure.

A single-use endoscope is disposed of (discarded) after being used once, and should not be used multiple times. Even a reusable endoscope capable of being used multiple times by being reprocessed can be stopped being used and be sent to the manufacturer or the like for maintenance after being used a predetermined number of times.

Therefore, the single-use endoscope can no longer be used after a single use. The reusable endoscope should not be used any more after being used a predetermined number of times.

The embodiment described below can provide an endoscope system, image generation method, and storage medium that allow a user to see that an endoscope should not be used when the number of times the endoscope is used becomes equal to or larger than a predetermined number of times.

An embodiment of the present disclosure will be described below with reference to the drawings. However, the present disclosure is not limited by the embodiment described below.

Note that in the drawings, the same or corresponding elements are denoted by the same reference signs as appropriate. Also, it should be noted that the drawings are schematic and that in a single drawing, length relationships among different elements, length ratios among different elements, or quantities of multiple elements may not be shown in their true relationships to one another for simplicity of explanation. Furthermore, length relationships or length ratios among different elements may not coincide with one another among different drawings.

First Embodiment

Figure 2:
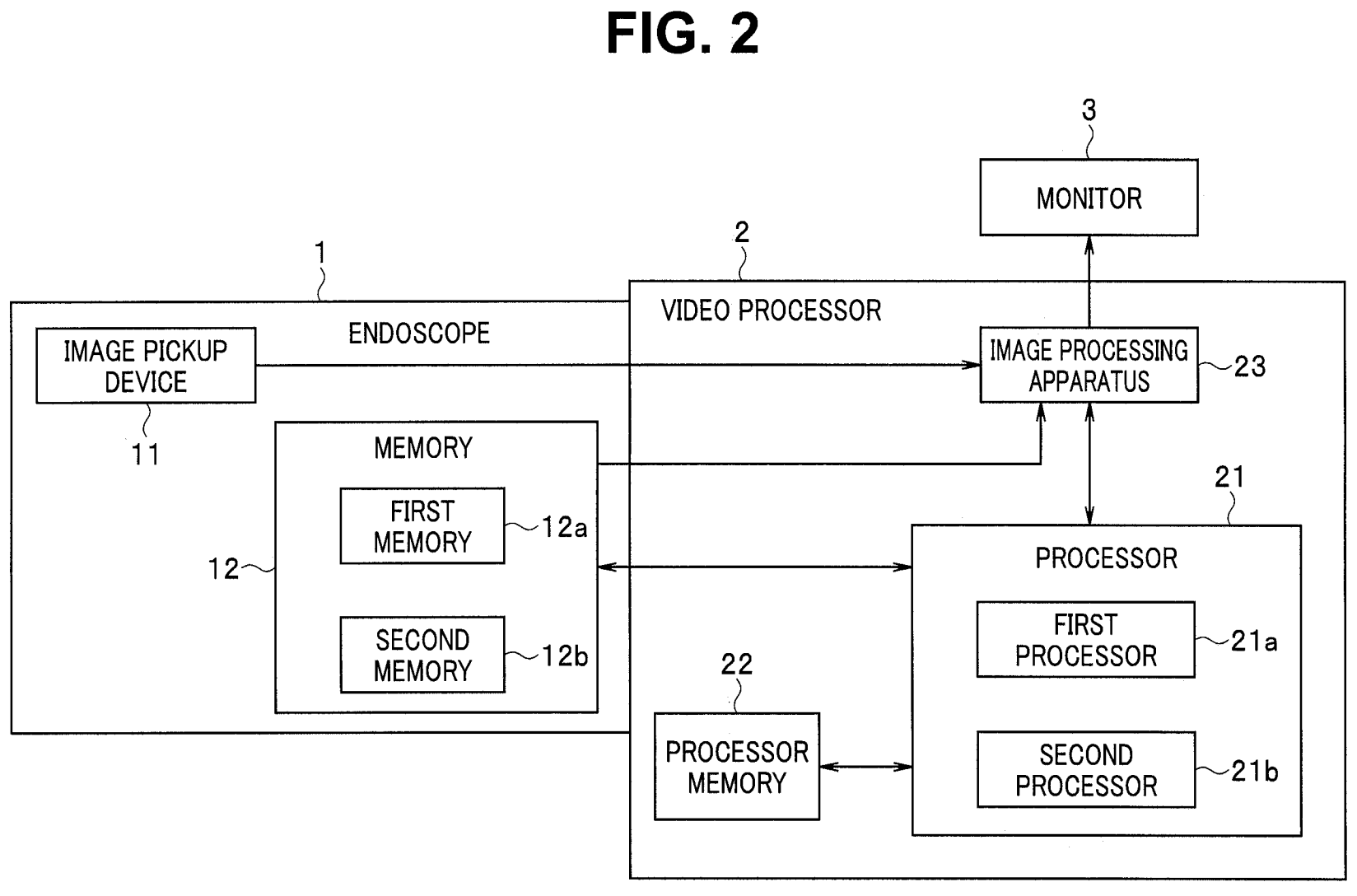

FIGS. 1 to 8 show a first embodiment of the present disclosure. FIG. 1 is a perspective view showing a configuration of an endoscope system according to the first embodiment. FIG. 2 is a block diagram showing an electrical configuration of the endoscope system according to the first embodiment.

As shown in FIGS. 1 and 2, the endoscope system includes an endoscope 1, a video processor 2, and a monitor 3.

The endoscope 1 may be a reusable endoscope capable of being used multiple times by being reprocessed. In that case, the endoscope 1 can be stopped being used and be sent to the manufacturer or the like for maintenance after being used a predetermined number of times.

Alternatively, the endoscope 1 may be a single-use endoscope discarded after being used once. The single-use endoscope is used only once and should not be used multiple times. Besides, the endoscope 1 may be a type, to an insertion portion of which a camera head is attached detachably.

The endoscope 1 includes an insertion portion 1*a*, an operation portion 1*b*, and a universal code 1*c*.

The insertion portion 1*a* is a part inserted into a subject or an object. The subject is assumed to be a living thing such as a human being or an animal. However, an object may be a non-living thing such as a machine or a building. The insertion portion 1*a* includes a distal end portion 1*a*1, a bending portion 1*a*2, and a flexible tubular portion 1*a*3 in order from a distal end side to a proximal end side.

The endoscope 1 is configured, for example, as an electronic endoscope, with an image pickup device 11 (see FIG. 2) provided in the distal end portion 1*a*1. The image pickup device 11 is an image sensor configured to photoelectrically convert (pick up) an optical image of the subject and transmit an image pickup signal. The image pickup device 11 is configured as a color image pickup device in which a plurality of pixels are arrayed two-dimensionally and, for example, a primary-color Bayer filter is placed on the pixels (however, a monochrome image pickup device may be adopted). The optical image of the subject is focused on the image pickup device 11 by an objective optical system. The image pickup signal obtained as a result of image pickup by the image pickup device 11 contains endoscopic image data. The endoscopic is configured to obtain the endoscopic image data obtained by the endoscope 1.

A signal line, a light guide, bending wires, a treatment instrument channel, and the like are disposed in the insertion portion 1*a*. The signal line is connected to the image pickup device 11. The signal line is disposed in the insertion portion 1*a*, the operation portion 1*b*, and the universal code 1*c*. The light guide transmits illumination light. The bending wires bend the bending portion 1*a*2 when pulled. The treatment instrument channel allows passage of endoscopic treatment instruments.

An illumination window, an observation window, and an opening on a distal end side of the treatment instrument channel are placed in a distal end face of the distal end portion 1*a*1. The illumination window illuminates the subject with illumination light transmitted through the light guide. The observation window allows the optical image of the subject to enter the objective optical system.

The bending portion 1*a*2 is capable of being actively bent, for example, in two directions or in four directions—up, down, left, and right. The bending portion 1*a*2 is disposed on the proximal end side of the distal end portion 1*a*1.

When the bending portion 1*a*2 is bent, the distal end portion 1*a*1 changes direction. This results in changes in image pickup direction of the image pickup device 11 and lighting direction of the illumination light from the light guide. The bending portion 1*a*2 is also bent to improve insertability of the insertion portion 1*a* in the subject.

The flexible tubular portion 1*a*3 has flexibility. The flexible tubular portion 1*a*3 is disposed on the proximal end side of the bending portion 1*a*2. Note that the endoscope 1 here is a flexible endoscope that includes the flexible tubular portion 1*a*3. However, the endoscope 1 may be a rigid endoscope that has a rigid tubular portion instead of the flexible tubular portion 1*a*3.

The operation portion 1*b* is used to operate the endoscope 1. The operation portion 1*b* is disposed on the proximal end side of the insertion portion 1*a*. The operation portion 1*b* includes a grasping portion 1*b*1, a bending operation knob 1*b*2, a plurality of operation buttons 1*b*3, and a treatment instrument insertion port 1*b*4.

The grasping portion 1*b*1 is used by an operator to grasp the endoscope 1 with his/her palm.

The bending operation knob 1*b*2 is an operation device used to bend the bending portion 1*a*2. The bending operation knob 1*b*2 is operated by, for example, the thumb of the hand grasping the grasping portion 1*b*1. When the bending operation knob 1*b*2 is turned, the bending wires are pulled and the bending portion 1*a*2 is bent.

The plurality of operation buttons 1*b*3 include, for example, an air/liquid feeding button, a suction button, and a button related to image pickup. The air/liquid feeding button is used to feed air/liquid to the observation window in the distal end portion 1a1 through a non-illustrated air/liquid feeding channel. The observation window is cleaned by liquid feeding and the liquid used for the cleaning is wiped off by air feeding.

The suction button is used to draw out liquids, mucous membranes, and the like from the subject. The suction from the subject is carried out, for example, through the treatment instrument channel that also serves as a suction channel. The button related to image pickup is, for example, a button switch for release operation.

The treatment instrument insertion port 1b4 is an opening on the proximal end side of the treatment instrument channel. Various types of treatment instruments such as forceps are inserted into the treatment instrument channel through the treatment instrument insertion port 1b4. A distal end portion of the inserted treatment instrument protrudes from the opening on the distal end side of the treatment instrument channel. Various types of treatment are performed using the distal end portion of the treatment instrument.

The universal code 1c is extended from a flank, for example, on the proximal end side of the operation portion 1b. The signal line, the light guide, the suction channel communicated with the treatment instrument channel, and the like, are disposed in the universal code 1c. A connector 1c1 is provided on an extending end of the universal code 1c. The connector 1c1 is connected to the video processor 2.

The video processor 2 is connected to the endoscope 1 and the monitor 3. The video processor 2 performs image processing on the image pickup signal received from the endoscope 1 and thereby generates an image signal. The video processor 2 transmits the generated image signal to the monitor 3. The video processor 2 also serves as, for example, a light source apparatus configured to supply illumination light. However, the light source apparatus may be formed separately from the video processor 2. The video processor 2 can include one or more of the imaging processor 23, the first processor 21a and the second processor 21b.

The monitor 3 receives the image signal from the video processor 2 and displays an endoscopic image.

As shown in FIG. 2, the endoscope 1 includes a memory 12. The memory 12 includes a nonvolatile first memory 12a and a nonvolatile second memory 12b.

The first memory 12a stores image correction data (first image correction data) unique to the endoscope 1. The second memory 12b stores information including the number of times the endoscope 1 is used. The endoscope 1 includes a second memory 12b, and the second memory 12b can store the information including the number of times the endoscope 1 is used.

In a configuration example shown in FIG. 2, the first memory 12a and the second memory 12b are one part and another part of the memory 12 formed integrally. The first memory 12a and the second memory 12b can be provided as part of a single memory unit.

Figure 3:
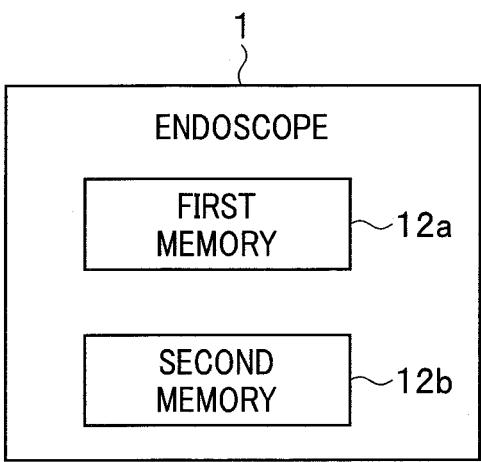
FIG. 3 is a block diagram showing another configuration example involving a first memory and a second memory in an endoscope according to the first embodiment.

FIG. 3 is a block diagram showing another configuration example involving the first memory 12a and the second memory 12b in the endoscope 1 according to the first embodiment. As shown in FIG. 3, the first memory 12a and the second memory 12b may be formed separately.

As shown in FIG. 2, the video processor 2 includes a processor 21, a processor memory 22, and an image processing apparatus 23 (imaging processor).

The processor memory 22 is a storage device that stores, in a nonvolatile manner, processing programs (computer programs) executed by the processor 21. Also, the processor memory 22 stores various parameters used for processing as well as user settings. Furthermore, the processor memory 22 may temporarily store image signals to be processed by the image processing apparatus 23.

Information stored by the processor memory 22 includes information such as image signals that can be stored temporarily and information such as processing programs that can be stored continuously. Therefore, the processor memory 22 can be configured to include a volatile memory and a nonvolatile memory.

The processor 21 includes hardware and is configured, for example, as an ASIC (application specific integrated circuit) including a CPU (central processing unit) or as an FPGA (field programmable gate array). The processor 21 executes processing programs read from the processor memory 22 and thereby achieves various functions. However, at least part of the processor 21 may be configured as a dedicated electronic circuit.

The processor 21 can include a first processor 21a and a second processor 21b. The first processor 21a functions as an instruction section configured to perform control and make determinations. The second processor 21b functions as an execution unit configured to overwrite the memory 12 of the endoscope 1, and so forth based on instructions from the first processor 21a. Functions of the first processor 21a and second processor 21b will be described in detail later along with operations of the video processor 2.

The processor 21 controls various parts in the video processor 2, including the image processing apparatus 23, according to the processing programs. The processor 21 reads and writes information from/to the processor memory 22.

Furthermore, by controlling the endoscope 1, the processor 21 drives the image pickup device 11 and reads and writes information from/to the memory 12. For example, the processor 21 controls timing to read from the image pickup device 11. Besides, based on brightness information about the subject obtained from the image pickup signal, the processor 21 controls exposure periods (charging periods of individual pixels) of the image pickup device 11.

The image processing apparatus 23 receives the image pickup signal transmitted from the image pickup device 11, through a signal line. Furthermore, the image processing apparatus 23 receives image correction data from the first memory 12a.

Using the image correction data, the image processing apparatus 23 performs various types of image processing (corrections) on the image pickup signal, including demosaicking, pixel defect correction, image region setting, white balance correction, noise correction, color correction, contrast correction, gamma correction, and pixel number conversion. A corrected image generated by the image processing apparatus 23 through image processing becomes a displayable image signal. The image processing apparatus 23 may superimpose various information such as character information or guide information on the image signal.

The image processing apparatus 23 includes hardware and may be configured as an ASIC including a CPU or as an FPGA, as with the processor 21. At least part of the image processing apparatus 23 may be configured as a dedicated electronic circuit.

FIG. 2 shows an example in which the first processor 21a and second processor 21b can be provided integrally in the processor 21 of the video processor 2. The first processor 21a and the second processor 21b can be provided as part of a single processor unit. However, the present configuration is not restrictive. Another configuration example involving the first processor 21a and the second processor 21b will be described with reference to FIGS. 4 to 7.

Figure 4:
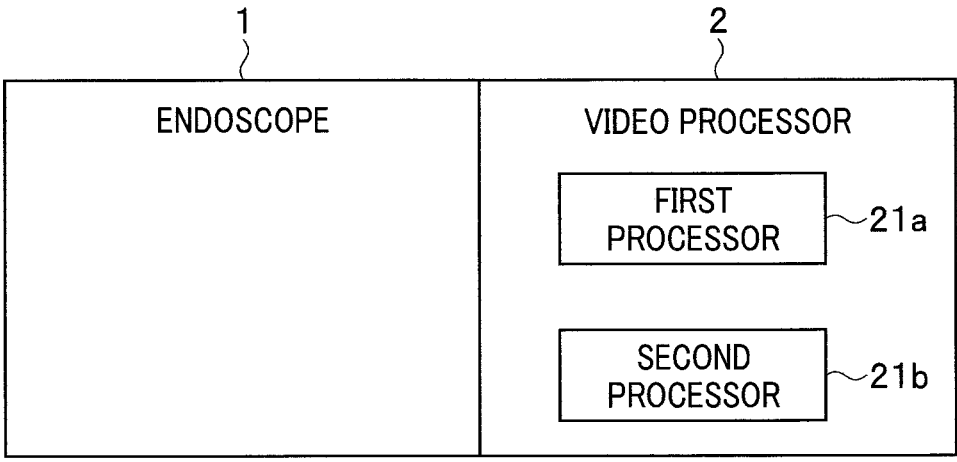
FIG. 4 is a block diagram showing an example in which a first processor and a second processor are provided separately in a video processor, according to the first embodiment.

FIG. 4 is a block diagram showing an example in which the first processor 21a and the second processor 21b are provided separately in the video processor 2, according to the first embodiment.

Figure 5:
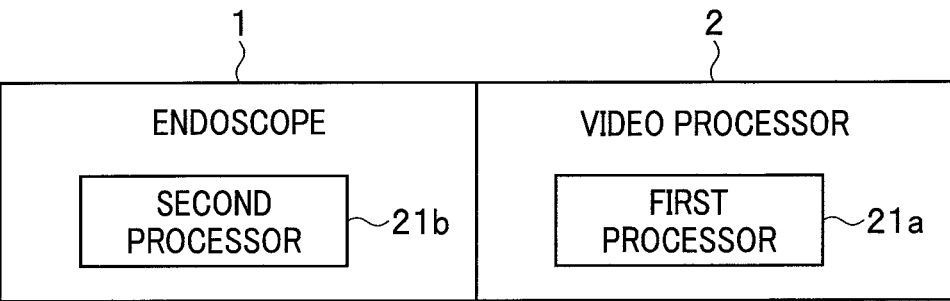
FIG. 5 is a block diagram showing an example in which a first processor is provided in the video processor and the second processor is provided in the endoscope, according to the first embodiment.

FIG. 5 is a block diagram showing an example in which the first processor 21a is provided in the video processor 2 and the second processor 21b is provided in the endoscope 1, according to the first embodiment. Naturally, the first processor 21a and the second processor 21b are provided separately.

Figure 6:
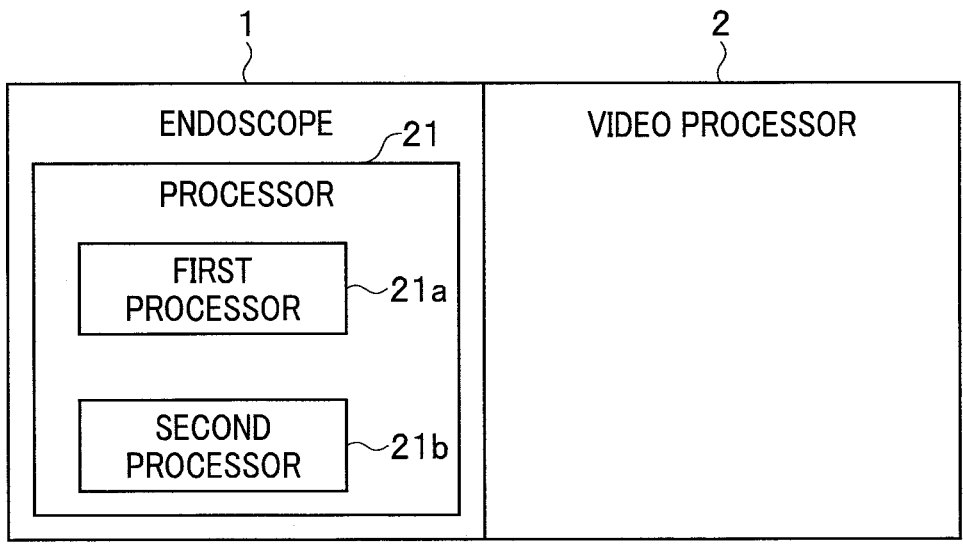
FIG. 6 is a block diagram showing an example in which a processor provided with the first processor and the second processor is provided in the endoscope, according to the first embodiment.

FIG. 6 is a block diagram showing an example in which the processor 21 provided with the first processor 21a and the second processor 21b is provided in the endoscope 1, according to the first embodiment. The first processor 21a and the second processor 21b are provided integrally in the processor 21.

Figure 7:
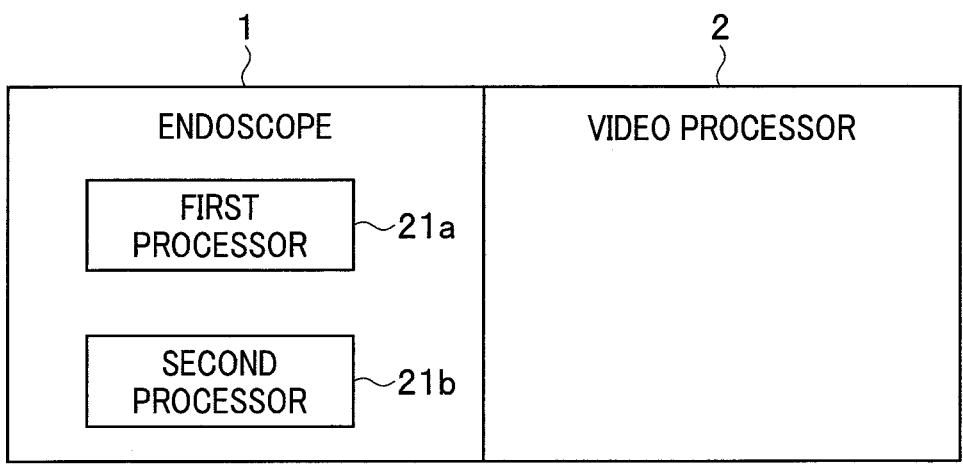
FIG. 7 is a block diagram showing an example in which the first processor and the second processor are provided separately in the endoscope, according to the first embodiment.

FIG. 7 is a block diagram showing an example in which the first processor 21a and the second processor 21b are provided separately in the endoscope 1, according to the first embodiment.

Note that any of the configurations shown in FIGS. 2 and 4 to 7 can be adopted, but this does not forbid a configuration in which the first processor 21a is provided in the endoscope 1 and the second processor 21b is provided in the video processor 2. The endoscope system can include the endoscope 1 can include one or more of the first processor 21a and the second processor 21b.

Figure 8:
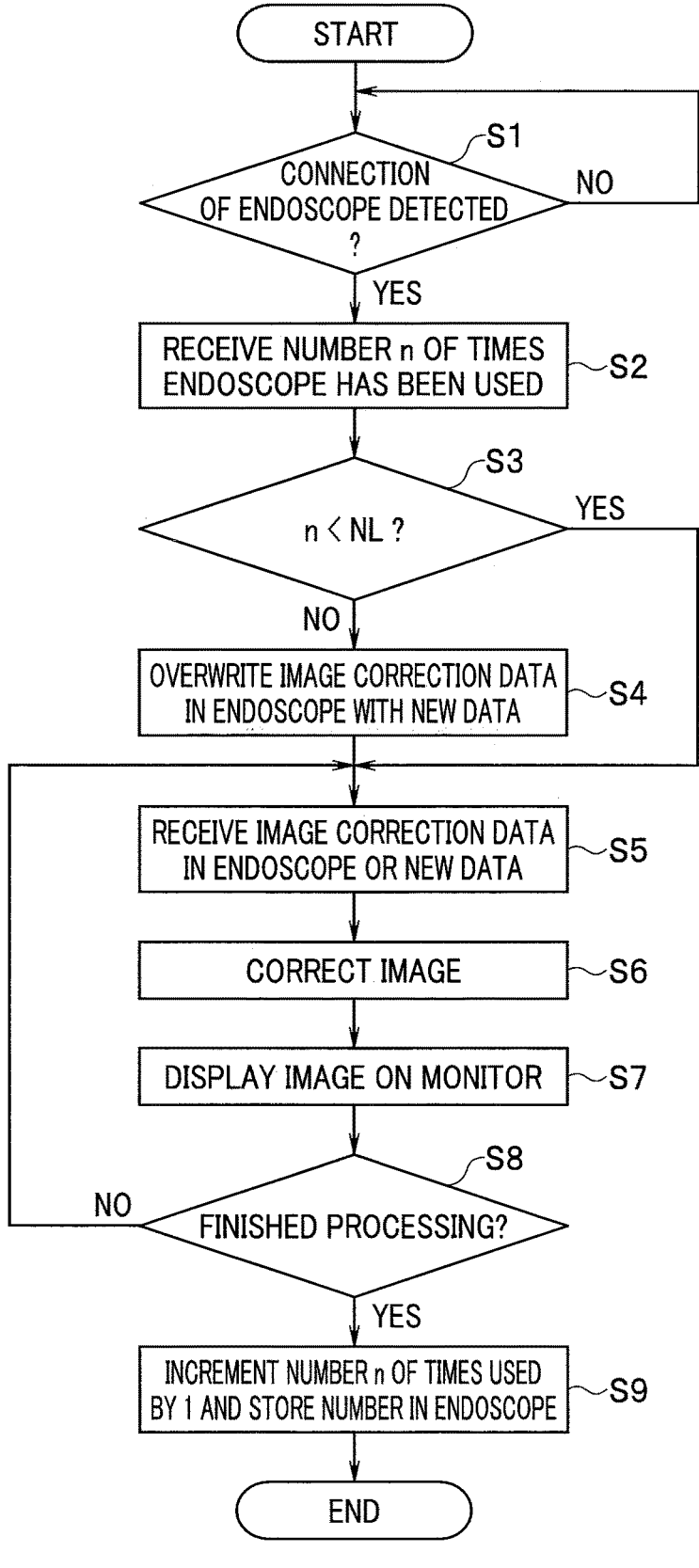
FIG. 8 is a flowchart showing operation of the video processor according to the first embodiment.

FIG. 8 is a flowchart showing operation of the video processor 2 according to the first embodiment.

When processing is started, the first processor 21a determines whether connection of the endoscope 1 to the video processor 2 has been detected (step S1). The connection of the endoscope 1 may be detected based on, for example, whether the first processor 21a has been enabled to read information from the memory 12. Alternatively, the connection of the endoscope 1 may be detected by detecting connection of the connector 1c1 using a connector receptacle of the video processor 2. However, this is not restrictive, and the connection of the endoscope 1 may be detected using any appropriate technique. The first processor 21a can detect a connection between the endoscope 1 and the imaging processor 23, and receive the information including the number of times the endoscope 1 is used from the second memory 12b.

When connection of the endoscope 1 is not detected, the first processor 21a waits until the endoscope 1 is connected by performing the process of step S1 at appropriate time intervals.

If connection of the endoscope 1 is detected in step S1, the first processor 21a receives information including the number of times the endoscope 1 has been used from the second memory 12b (step S2). It is assumed here that the number of times used thus received is n.

The first processor 21a compares the number n of times used, with a predetermined number NL of times and thereby determines whether the number n of times used is smaller than the predetermined number NL of times (step S3). The first processor 21a is configured to determine if the number of times the endoscope 1 is used is equal to or larger than the predetermined number of times NL. The predetermined number NL of times is 1 if the endoscope 1 is a single-use endoscope. On the other hand, if the endoscope 1 is a reusable endoscope, the predetermined number NL of times is a predetermined number which is set as a number of times at which the endoscope 1 can be set for maintenance and is equal to or larger than 1.

Here, if it is determined that the number n of times used is not smaller than the predetermined number NL of times (is equal to or larger than the predetermined number NL of times), the first processor 21a gives an instruction to overwrite image correction data. In response to the instruction from the first processor 21a, the second processor 21b overwrites the image correction data (first image correction data) in the first memory 12a with new data (second image correction data) different from the image correction data (step S4). The second processor 21b is configured to overwrite the first image correction data with the second image correction data when the first processor 21a determines the number of times the endoscope is used is equal to or larger than the predetermined number of times NL. The endoscope 1 can include the first memory 12a, and the first memory 12a can store one of the first image correction data and the second image correction data.

The new data here is such data that corrected image obtained by correcting endoscopic image data using the new data will not become a normal image. A visibility of the first image is a first visibility, and a visibility of the second image is a second visibility, and the first visibility is higher than the second visibility.

As a concrete example, the new data may include at least one of (1) new data on pixel defect correction, (2) new data on read timing, (3) new data on image region setting, (4) new data on white balance, or (5) new data on exposure periods.

The imaging processor 23 is configured to at least one of (1) obtain the second image including a normal pixel designated as a defective pixel, (2) shift a timing to read the endoscopic image from a timing to read the endoscopic image to obtain the first image, (3) obtain the second image to be smaller or larger than the first image, (4) obtain the second image including a white balance different from a white balance of the first image, and (5) obtain the second image by using the endoscopic image obtained by maximized an exposure period.

(1A) Normal pixel defect correction data (image correction data) gives coordinates of defective pixels in the image pickup device 11. The coordinates of defective pixels have been found in advance through calibration and the like. The defective pixels have bright dot defects which appear bright in dark state, dark dot defects which appear dark in the presence of incident light, or the like. The image processing apparatus 23 performs a pixel defect correction process to perform interpolation calculations on pixel values of defective pixels using pixel values of normal pixels of the same color existing around the defective pixels.

(1B) New data on pixel defect correction is configured as data that designates normal pixels of the image pickup device 11 as defective pixels. A concrete example is data that designates 70% (a numerical example) of pixels in an image pickup region of the image pickup device 11 as defective pixels. A pixel defect correction process is performed by the image processing apparatus 23 in a manner similar to (1A). Thus, a pixel defect correction process performed using the new data results in an image with a greatly reduced resolution. Consequently, by watching the monitor 3, the user can recognize at once that the endoscope 1 is not serviceable.

A pixel of the obtained second image is designated as the defective pixel that is in a state of pixel saturation (white or black, etc.). The first visibility is higher than the second visibility since the pixel of the first image is performed interpolation calculations and has less defective pixel than the second image.

(2A) Data on normal read timing (image correction data) gives image pickup signal read timing optimized according to length of the signal line connected to the image pickup device 11. The signal line is disposed in the insertion portion 1*a*, the operation portion 1*b*, and the universal code 1*c* as described above and has a total length corresponding to lengths of the mentioned parts. The data on normal read timing allows the image pickup signal to be read normally.

(2B) The new data on read timing is obtained by shifting the timing to read the image pickup signal (endoscopic image data) from normal timing. An example of such data is timing data corresponding to a signal line differing in length from (longer or shorter than) an actual signal line. When the image pickup signal is read using the new data, either no image can be acquired at all or only fragmentary images can be acquired, i.e., a normal image cannot be acquired. Thus, by watching the monitor 3, the user can recognize at once that the endoscope 1 is not serviceable.

The first image is obtained from the endoscope 1 at a first timing, the second image is obtained from the endoscope 1 at a second timing, and the first timing is different from the second timing. For example, second image can be includes one or more of (i) a pixel of the obtained second image can be designated as the defective pixel that is in a state of pixel saturation (white or black, etc.), (ii) black areas at the top, bottom, left, and right edges of the image, and (iii) an image that appear to be shifted vertically or horizontally without moving the scope. The first image can be a normal endoscopic image that a user can recognize what is captured. The second image can be an abnormal endoscopic image that the user can difficultly recognize what is captured. Therefore, the first visibility can be higher than the second visibility.

(3A) Normal image region setting data (image correction data) is used to set a display region to be displayed on the monitor 3 out of an entire region of an image acquired from the image pickup device 11. To give an example, the display region is set to a region occupying 95% of the area of the entire region.

(3B) The new data on image region setting is obtained by setting a display region in the endoscopic image data smaller than a usual display region. To give an example, the display region in the new data is set to a region occupying 47.5% area of the entire region (i.e., half the display region (95%) based on the normal image region setting data). In this case, only part of the image is displayed on the monitor 3, allowing the user to recognize at once that the endoscope 1 is not serviceable.

The obtained first image has a first size, the obtained second image has a second size, and the first size is different from the second size. The first image can be displayed to be seen almost whole of image or to be recognized what is captured. The second image can be displayed to be seen only a part of the second image, be smaller than the first image or be larger than the first image. The first visibility is higher than the second visibility.

(4A) Normal white balance data (image correction data) is data on a color signal set in advance as a target value of white balance. The normal white balance data is set, for example, according to spectral characteristics of a primary-color Bayer filter used in the image pickup device 11.

(4B) The new data on white balance is obtained by varying the white balance of the endoscopic image data from usual white balance. As the new data on white balance, a color signal deviating greatly from a color signal of the target value of the white balance is set. Consequently, an image differing greatly in color from a usual image is displayed on the monitor 3, allowing the user to recognize at once that the endoscope 1 is not serviceable.

The obtained first image has a first white balance, the obtained second image has a second white balance, and the first white balance is different from the second white balance. The first visibility is higher than the second visibility.

(5A) Normal exposure period data (image correction data) indicates correspondence between luminance of the subject and an exposure period. Generally, the higher the luminance of the subject, the shorter the exposure period. The exposure period of the image pickup device 11 is defined by an electronic shutter and is a time interval from when a charge of each pixel is reset to when the pixel is read out.

(5B) The new data on exposure periods is obtained by setting the exposure periods used in acquiring the endoscopic image data to a maximum exposure period without relying on the luminance of the subject. The maximum exposure period is a maximum value of the exposure period that can be set according to a frame rate (such as 30 fps or 60 fps). Consequently, for example, an image affected by halation is displayed on the monitor 3, allowing the user to recognize at once that the endoscope 1 is not serviceable.

The obtained first image has a first exposure, the obtained second image has a second exposure, and the first exposure is different from the second exposure. The second image can include more than half white pixels, or all white pixels, more than half black pixels or all black pixels. The first image can be recognized what is captured. The second image can include halation. The first visibility is higher than the second visibility.

Whereas a few examples of new data have been shown above, needless to say, the present disclosure is not limited to these examples. For example, the new data may be erased data for use to erase image correction data. A concrete example of erase data is data in which bit values of all bits making up the erase data are 0. Even if endoscopic image data is corrected with erase data, no endoscopic image is displayed in the corrected image and a black screen appears on the monitor or a message image appears indicating that image display is disabled. Thus, the erase data does not make the corrected image a normal image either.

If it is determined in step S3 that the number n of times used is smaller than the predetermined number NL of times, the first processor 21*a* does not give an instruction to overwrite image correction data and the process of step S4 is skipped.

If it is determined in step S3 that the number n of times used is smaller than the predetermined number NL of times, the first processor 21*a* gives an instruction to transmit the image correction data to the image processing apparatus 23 of the video processor 2. Besides, if the process of step S4 is performed based on the determination that the number n of times used is equal to or larger than the predetermined number NL of times, the first processor 21*a* gives an instruction to transmit new data to the image processing apparatus 23.

In this way, depending on whether the number n of times used is equal to or larger than the predetermined number NL of times, the image processing apparatus 23 receives either the image correction data stored in the first memory 12*a* or the new data (step S5). When the first processor 21*a* determines the number of times the endoscope 1 is used is smaller than the predetermined number of times NL, the imaging processor 23 is configured to receive the first image correction data, and obtain a first image based on the endoscopic image data by using the received first image correction data. When the first processor 21a determines the number of times the endoscope is used is equal to or larger than the predetermined number of times, the imaging processor 23 is configured to receive the second image correction data, and obtain a second image based on the endoscopic image data by using the received second image correction data.

If image correction data is received from the first memory 12a, the image processing apparatus 23 corrects the endoscopic image data using the image correction data and thereby generates a corrected image. On the other hand, if new data is received from the first memory 12a, the image processing apparatus 23 corrects the endoscopic image data using the new data and thereby generates a corrected image (step S6).

The image processing apparatus 23 transmits an image signal of the corrected image thus generated to the monitor 3. The monitor 3 receives the image signal from the video processor 2 and displays the image. In so doing, the image signal corrected with the image correction data is displayed on the monitor 3 as a usual endoscopic image. On the other hand, the image signal corrected with the new data is displayed on the monitor 3 as an abnormal image, or a message image or the like appears indicating that image display is disabled (step S7).

Subsequently, the first processor 21a determines whether to finish processing (step S8), and if it is determined that the processing is not to be finished, the first processor 21a returns to step S5 and performs the process described above.

Note that if the image correction data or new data read out for the first image frame can be used as it is for the second and subsequent image frames, the processing may return to step S6 instead of step S5 after step S8.

On the other hand, if it is determined in step S8 that the processing is to be finished, the first processor 21a gives an instruction to increment the number n of times used which is stored in the second memory 12b by one, overwrite the current number n of times used with the incremented number, and store the resulting number in the second memory 12b.

In response to the instruction from the first processor 21a, the second processor 21b overwrites the numerical value of the number n of times used in the second memory 12b (step S9). Consequently, when the endoscope 1 is connected to the video processor 2 next time, the number of times larger by one than the current value will be compared with the predetermined number NL of times.

If it is determined in step S3 that that the number n of times used is equal to or larger than the predetermined number NL of times, the process of step S9 may be omitted.

Once the process of step S9 is performed in this way, the processing in FIG. 8 is finished.

Whereas it is assumed above that the number of times used is 0 or a natural number equal to or larger than 1, the number of times used may be counted by a method that does not use natural numbers (decimal number). For example, using binary numbers made up of multiple digits (the use of four digits is shown as an example), zero times, once, twice, and three times may be counted as "0000", "0001," "0010," and "0011," respectively. Alternatively, using the alphabet, 0 times, once, twice, and three times may be counted as "z," "a," "b," and "c," respectively. In this way, the counting method is not limited to natural numbers.

Since the first embodiment described above allows the user to see that the endoscope should not be used when the number of times the endoscope 1 is used becomes equal to or larger than the predetermined number NL of times, the user can stop the use of the endoscope 1 appropriately.

This makes it possible to prevent the user from using a single-use endoscope two or more times by mistake. In the case of a reusable endoscope, because the user can see when the endoscope should not be used any more, the user can send the endoscope 1 to the manufacturer or the like for maintenance before a failure occurs. This makes it possible to avoid downtime caused if the endoscope 1 is suddenly rendered unusable due to a failure.

Second Embodiment

Figure 9:
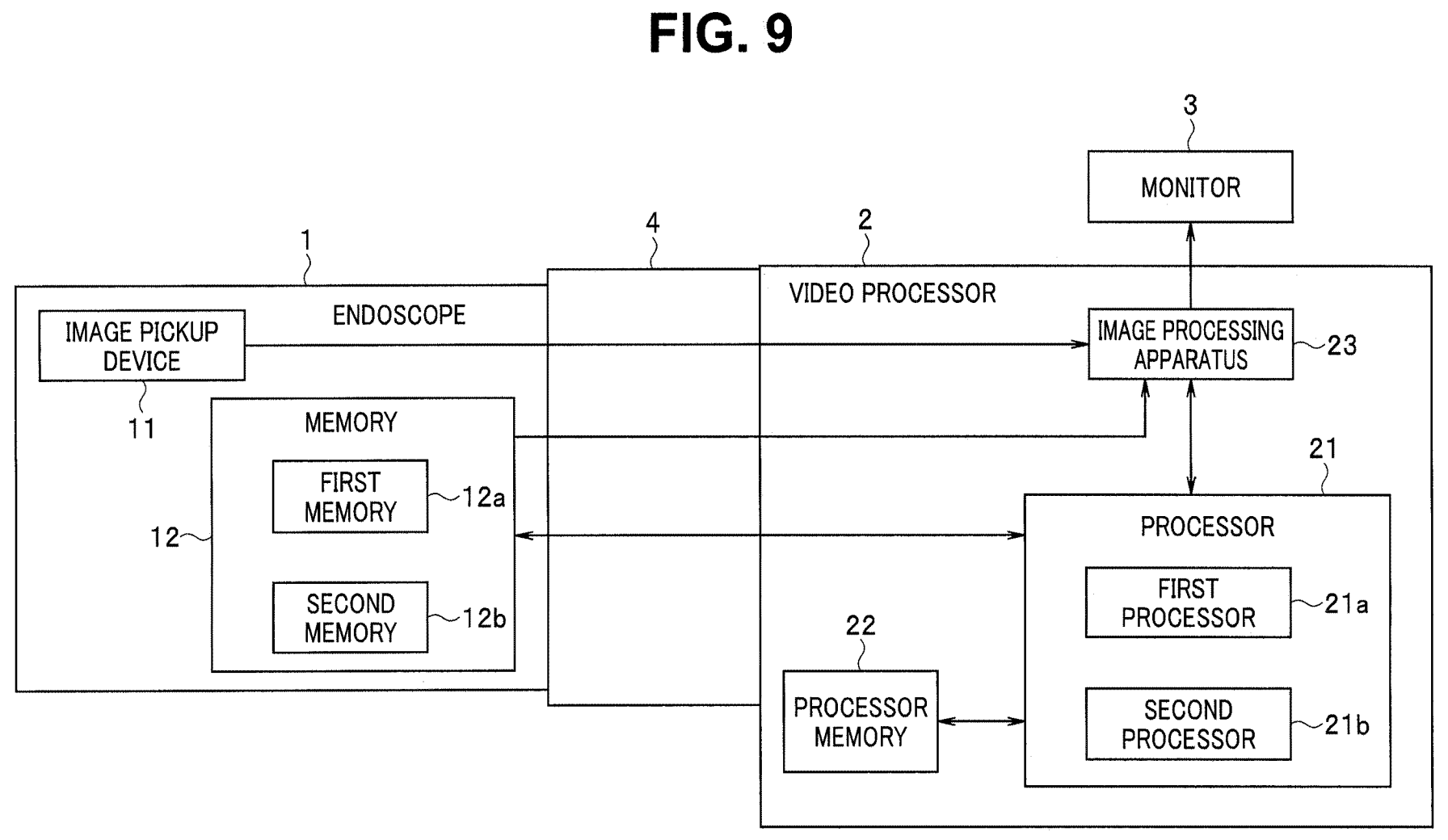

FIGS. 9 to 13 show a second embodiment of the present disclosure. FIG. 9 is a block diagram showing an electrical configuration of an endoscope system according to the second embodiment. In the second embodiment, parts that are similar to those in the first embodiment are denoted by the same reference signs, and explanations are omitted as appropriate. In the second embodiment, points that differ from the first embodiment are mainly explained.

The endoscope system according to the second embodiment includes an endoscope 1, a video processor 2, a monitor 3, and an adapter 4. The endoscope 1 is connected to the video processor 2 through the adapter 4. In other words, the adapter 4 is connected to the endoscope 1 and the video processor 2. The adapter 4 is an apparatus that ensures compatibility of connection between various models of the endoscope 1 and the video processor 2.

For example, suppose an aspect in which the arrangement and the number of connection pins of the connector 1c1 of the endoscope 1 differ depending on the model of endoscope 1. In this case, the adapter 4 has a structure that allows the arrangement and the number of the connection pins of any model of the endoscope 1. This structure enables the adapter 4 to connect various models of the endoscope 1 to the video processor 2.

The adapter 4 has a function of mediating the mechanical and electrical connection between the endoscope 1 and the video processor 2. The adapter 4 may be equipped with a third processor that has different functions than those of the first processors 21a and the second processor 21b, such as a function of A/D conversion, a function of performing part of image signal processing, and a function of driving the endoscope 1. The adapter 4 can be connected to the endoscope 1 and the imaging processor 23. The second processor 21b can be provided the adapter 4.

Figure 10:
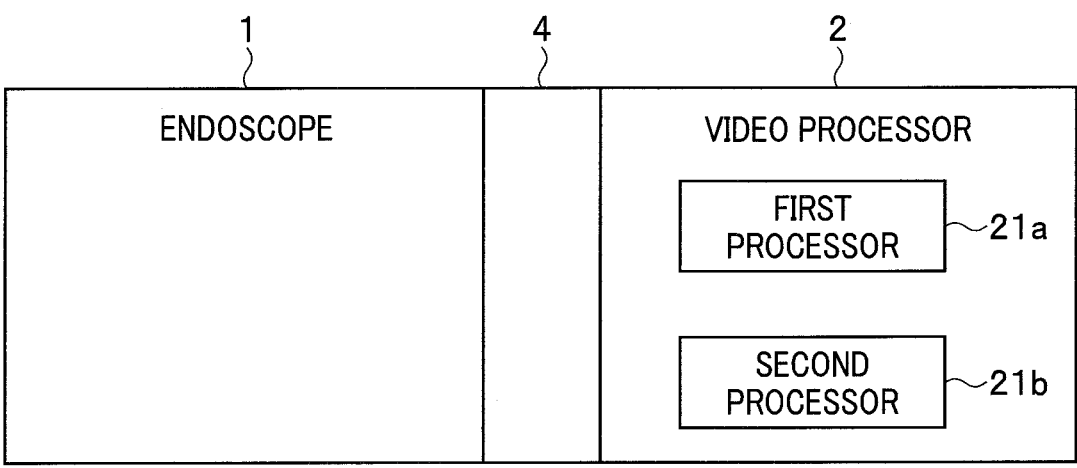
FIG. 10 is a block diagram showing an example in which a first processor and a second processor are provided separately in a video processor, according to the second embodiment.
Figure 11:
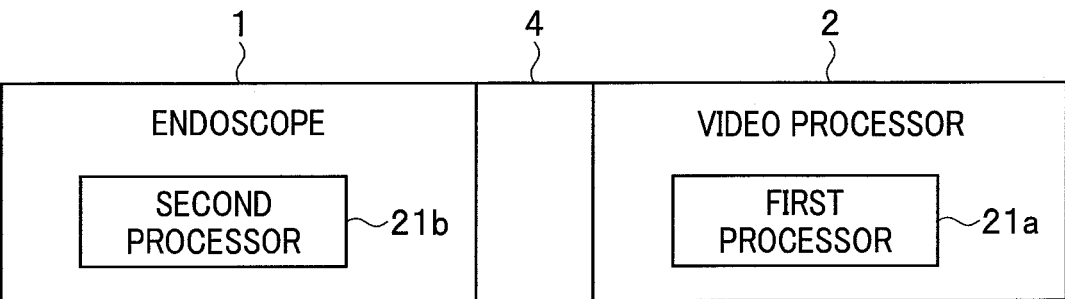
FIG. 11 is a block diagram showing an example in which a first processor is provided in the video processor and the second processor is provided in the endoscope, according to the second embodiment.
Figure 12:
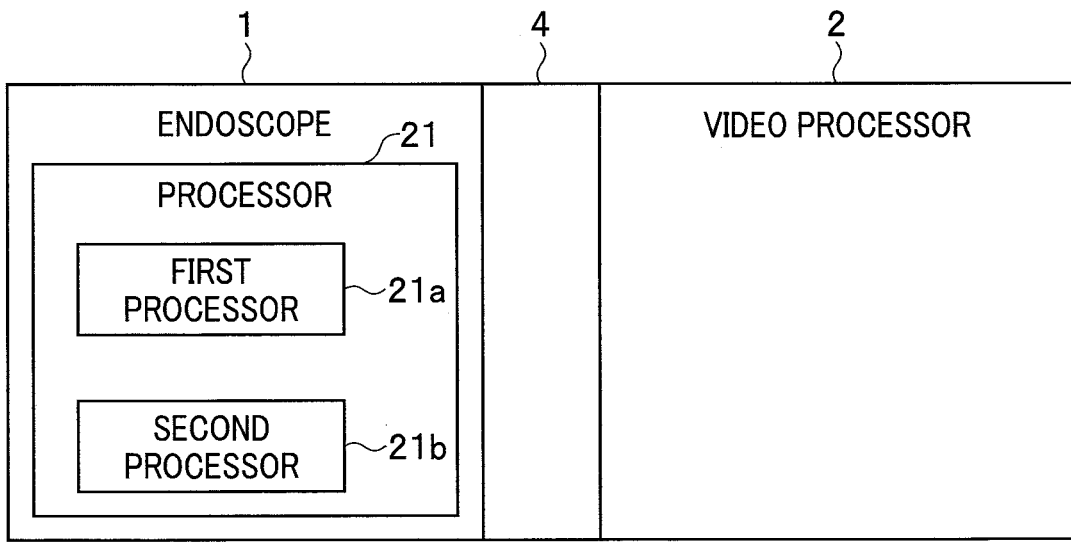
FIG. 12 is a block diagram showing an example in which a processor provided with the first processor and the second processor is provided in an endoscope, according to the second embodiment.
Figure 13:
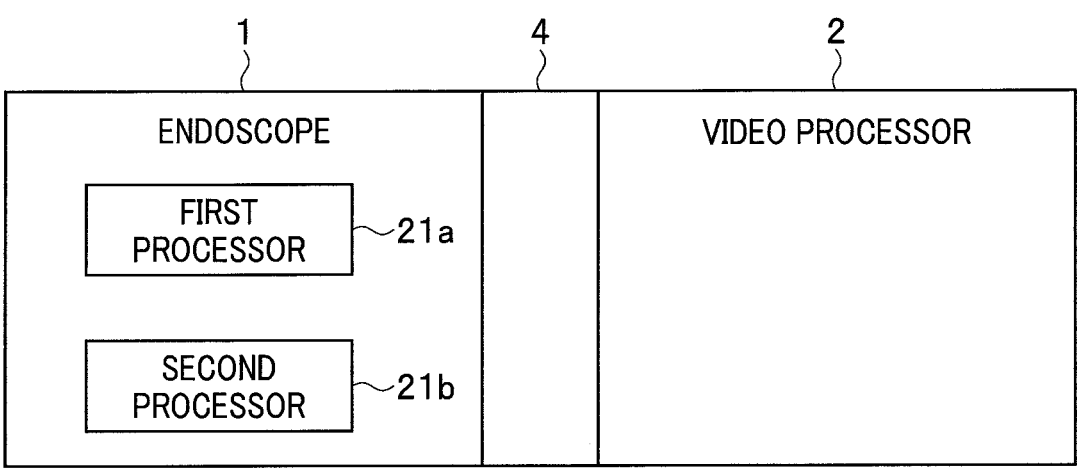
FIG. 13 is a block diagram showing an example in which the first processor and the second processor are provided separately in the endoscope, according to the second embodiment.

FIG. 10 is a block diagram showing an example in which the first processor 21a and the second processor 21b are provided separately in the video processor 2, according to the second embodiment. FIG. 11 is a block diagram showing an example in which the first processor 21a is provided in the video processor 2 and the second processor 21b is provided in the endoscope 1, according to the second embodiment. FIG. 12 is a block diagram showing an example in which the processor 21 provided with the first processor 21a and the second processor 21b is provided in the endoscope 1, according to the second embodiment. FIG. 13 is a block diagram showing an example in which the first processor 21a and the second processor 21b are provided separately in the endoscope 1, according to the second embodiment.

According to the second embodiment, the first processor 21a and the second processor 21b are placed in the endoscope 1 or in the video processor 2 as in the first embodiment, but not placed in the adapter 4.

The second embodiment has a similar effect as in the first embodiment. Furthermore, the second embodiment has the cost advantage that various models of the endoscope 1 can be connected to the video processor 2 and many models of the endoscope 1 can be used with only one video processor 2.

Third Embodiment

Figure 14:
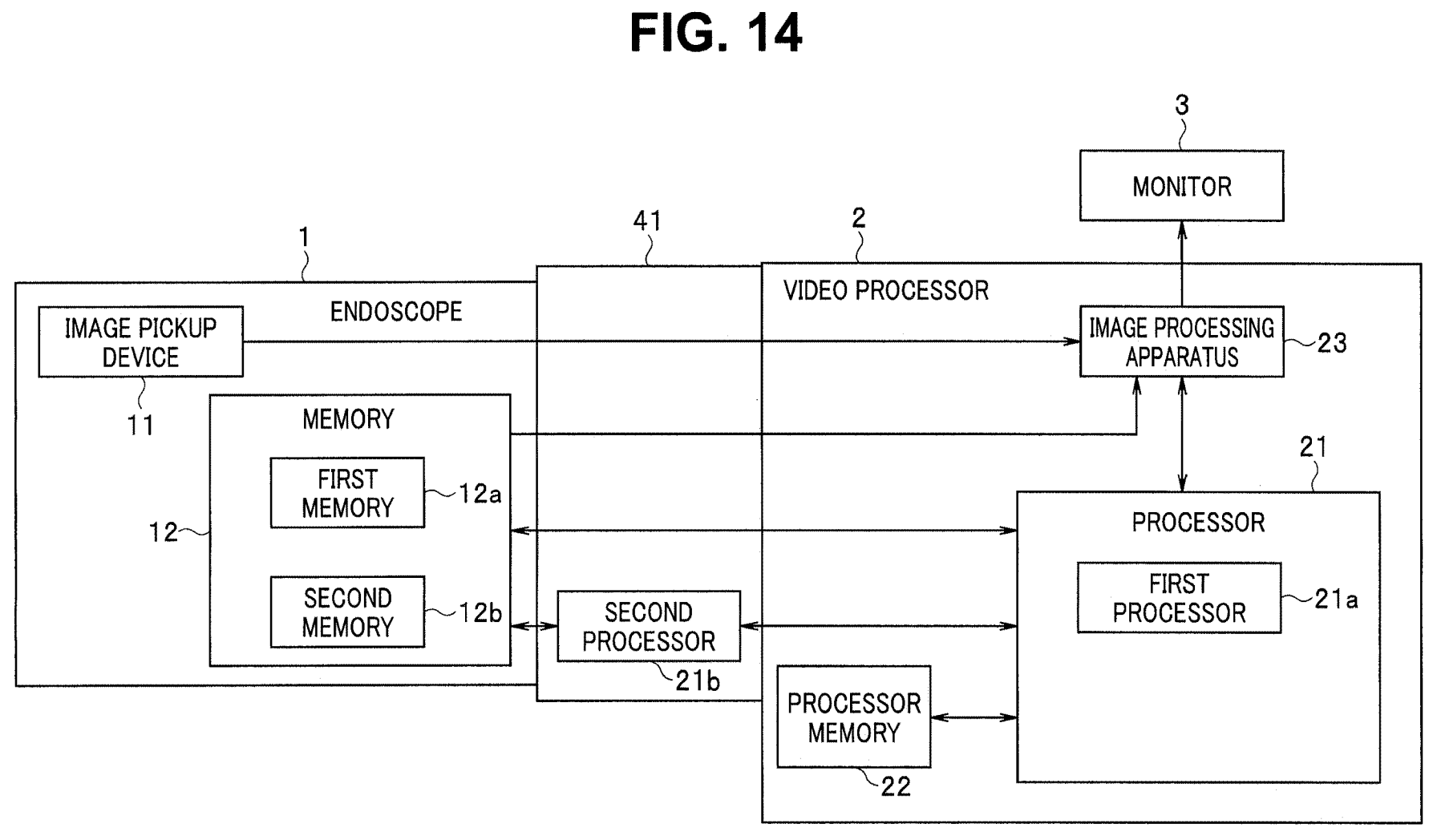

FIG. 14 shows a third embodiment of the present disclosure. FIG. 14 is a block diagram showing an electrical configuration of an endoscope system according to the third embodiment. In the third embodiment, parts that are similar to those in the first and second embodiments are denoted by the same reference signs, and explanations are omitted as appropriate. In the third embodiment, points that differ from the first and second embodiments are mainly explained.

The endoscope system according to the third embodiment includes an endoscope 1, a video processor 2, a monitor 3, and an adapter 41. The endoscope 1 is connected to the video processor 2 through the adapter 41. In other words, the adapter 41 is connected to the endoscope 1 and the video processor 2. The adapter 41 is an apparatus that ensures compatibility of connection between various models of the endoscope 1 and the video processor 2.

For example, suppose that the arrangement and the number of connection pins of the connector 1*c*1 of the endoscope 1 differ depending on the model of endoscope 1. In this case, the adapter 41 has a structure that allows the arrangement and the number of the connection pins of any model of the endoscope 1. This structure enables the adapter 41 to connect various models of the endoscope 1 to the video processor 2.

The adapter 41 has a function of mediating the mechanical and electrical connection between the endoscope 1 and the video processor 2. The adapter 4 according to the second embodiment does not have the second processor 21*b*. In contrast, the adapter 41 according to the third embodiment has the second processor 21*b*.

Thus, in the configuration of the third embodiment shown in FIG. 14, the first processor 21*a* is provided in the video processor 2 and the second processor 21*b* is provided in the adapter 41. The second processor 21*b* functions as an execution unit configured to overwrite the memory 12 of the endoscope 1, and so forth based on instructions from the first processor 21*a*, as in the first embodiment. The adapter 4 can be connected to the endoscope 1 and the imaging processor 23. The second processor 21*b* can be provided the adapter 4.

Specifically, in response to the instruction from the first processor 21*a*, the second processor 21*b* overwrites the image correction data in the first memory 12*a* with new data different from the image correction data (see step S4 in FIG. 8). Additionally, in response to the instruction from the first processor 21*a*, the second processor 21*b* overwrites the numerical value of the number n of times used in the second memory 12*b* (see step S9 in FIG. 8).

The adapter 41 may be further equipped with a third processor that has different functions than those of the first processors 21*a* and the second processor 21*b*, such as a function of A/D conversion, a function of performing part of image signal processing, and a function of driving the endoscope 1.

Third embodiment has an almost similar effect as in the first and second embodiments described above. Furthermore, according to the third embodiment, even if specifications of at least one of the first memory 12*a* and the second memory 12*b* in the endoscope 1 are changed as the technology progresses, the adapter 41 alone can be updated to address changes in the specifications of the memory 12.

In other words, by updating the adapter 41 alone, the endoscope 1 can be connected to the video processor 2 to perform predetermined processing by the first processor 21*a* and the second processor 21*b*. Thus, the endoscope system according to the third embodiment can address changes in the specifications of the memory 12 without changing the configurations of the endoscope 1 and the video processor 2, which has the cost advantage.

Although, in the third embodiment, the first processor 21*a* is provided in the video processor 2 and the second processor 21*b* is provided in the adapter 41, the third embodiment may have the following configuration. For example, the first processor 21*a* may be provided in the adapter 41 and the second processor 21*b* be provided in the video processor 2. Alternatively, the first processor 21*a* and the second processor 21*b* may be provided in the adapter 41.

In none of the above-mentioned configurations described with respect to the third embodiment, the first processor 21*a* or the second processor 21*b* is not placed in the endoscope 1. Thus, the third embodiment has the cost advantage that the endoscope 1 can be manufactured at a lower cost.

According to the above-mentioned configurations described, the endoscope system can be processor 21 or the first processor 21*a* and second processor 21*b*. The processor 21, or the first processor 21*a* and second processor 21*b* can be provided at one or more of the endoscope, the video processor, and the adapter. According to the above-mentioned configurations described, the endoscope system can include an endoscope 1 and a video processor 2. The endoscope system can be defined separately from the endoscope 1. In this case, the endoscope system does not include the endoscope 1. On the other hand, the endoscope system can be defined separately from the video processor. In this case, the endoscope system does not include the video processor.

Whereas description has mainly been given above by assuming that the present disclosure is an endoscope system, this is not restrictive, and the present disclosure may be an image generation method that generates images similarly to the endoscope system. Also, the present disclosure may be a computer program that causes a computer to perform processes similar to the processes of the endoscope system. Furthermore, the present disclosure may be a computer-readable non-transitory storage medium or the like that stores the computer program.

The image generation method comprises receiving information including the number of times the endoscope 1 is used, and determining if the number of times the endoscope is used is equal to or larger than the predetermined number of times. When the number of times the endoscope 1 is used is equal to or larger than the predetermined number of times, the method further comprises overwriting the first image correction data with the second image correction data. When the number of times the endoscope 1 is used is equal to or larger than the predetermined number of times, the method further comprises receiving the second image correction data from the endoscope, and obtaining the second image by using the second image correction data. The image generation method further comprises determining if the number of times the endoscope 1 is used is smaller than the predetermined number of times. When the number of times the endoscope is used is smaller than the predetermined number of times, the method further comprises receiving the first image correction data from the endoscope 1, and obtaining a first image by using the first image correction data.

The non-transitory computer-readable medium having instructions stored thereon, which when implemented by the processor causes the processor to execute a method. The method comprising receiving information including the number of times the endoscope 1 is used, comparing the number of times the endoscope 1 is used to a predetermined number of times. When comparing determines the number of times the endoscope is used is equal to or larger than the predetermined number of times, overwriting the first image correction data with the second image correction data, where the second image correction data is different from the first image correction data. When comparing determines the number of times the endoscope 1 is used is equal to or larger than the predetermined number of times, the method further includes receiving the second image correction data from the endoscope 1, and obtaining the second image by using the second image correction data. When comparing determines the number of times the endoscope 1 is used is smaller than the predetermined number of times, the method further includes receiving the first image correction data from the endoscope; and obtain the first image by using the first image correction data.

The present disclosure is not limited to the precise embodiment described above and may be embodied by changing components in the implementation stage without departing from the gist of the disclosure. Various aspects of the disclosure can be implemented using appropriate combinations of the components disclosed in the above embodiment. For example, some of all the components disclosed in the embodiment may be deleted. Furthermore, components may be combined as appropriate across different embodiments. Thus, various alterations and applications are possible without departing from the gist of the disclosure.

Example 1. An endoscope system comprising:
    an endoscope that includes a first memory configured to store image correction data unique to the endoscope, and a second memory configured to store information about a number of times the endoscope is used, the endoscope transmitting endoscopic image data obtained by image pickup;
    a video processor connected with the endoscope and configured to receive and process the endoscopic image data;
    a first processor including hardware and configured to receive the information about the number of times used, compare the number of times used with a predetermined number of times, and give an instruction to overwrite the image correction data when the number of times used is equal to or larger than the predetermined number of times; and
    a second processor including hardware and configured to overwrite the image correction data in the first memory with new data different from the image correction data in response to the instruction, wherein
    when the number of times used is equal to or larger than the predetermined number of times, the video processor receives the new data from the first memory, corrects the endoscopic image data using the new data, and thereby generates a corrected image.
Example 2. The endoscope system according to Example 1, wherein the first processor is provided in the video processor.
Example 3. The endoscope system according to Example 2, wherein the second processor is provided in the video processor.

Example 4. The endoscope system according to Example 3, wherein the first processor and the second processor are provided integrally.
Example 5. The endoscope system according to Example 2, wherein the second processor is provided in the endoscope.
Example 6. The endoscope system according to Example 1, wherein the first processor and the second processor are provided in the endoscope.
Example 7. The endoscope system according to Example 6, wherein the first processor and the second processor are provided integrally.
Example 8. The endoscope system according to Example 1, wherein the first memory and the second memory are one part and another part of a memory formed integrally.
Example 9. The endoscope system according to Example 1, wherein the first memory and the second memory are formed separately.
Example 10. The endoscope system according to Example 1, further comprising an adapter configured to be connected to the endoscope and the video processor, wherein
    at least one of the first processor or the second processor is provided in the adapter.
Example 11. The endoscope system according to Example 1, wherein the first processor detects when the endoscope is connected to the video processor and receives the information about the number of times used, from the second memory.
Example 12. The endoscope system according to Example 1, wherein when the number of times used is smaller than the predetermined number of times, the video processor receives the image correction data from the first memory, corrects the endoscopic image data using the image correction data, and thereby generates the corrected image.
Example 13. The endoscope system according to Example 12, wherein when the number of times used is smaller than the predetermined number of times, the first processor gives an instruction to transmit the image correction data to the video processor.
Example 14. The endoscope system according to Example 1, wherein when the number of times used is equal to or larger than the predetermined number of times, the first processor gives an instruction to transmit the new data to the video processor.
Example 15. The endoscope system according to Example 1, wherein the new data is such data that the corrected image obtained by correcting the endoscopic image data using the new data does not become a normal image.
Example 16. The endoscope system according to Example 15, wherein the new data includes at least one of:
    new data for pixel defect correction that designates a normal pixel as a defective pixel;
    new data on read timing obtained by shifting timing to read the endoscopic image data from normal timing;
    new data on image region setting obtained by setting a display region in the endoscopic image data smaller than a usual display region;
    new data on white balance obtained by varying white balance of the endoscopic image data from usual white balance; or
    new data on an exposure period obtained by setting an exposure period used in acquiring the endoscopic image data to a maximum exposure period without relying on luminance of the subject.

Example 17. An image generation method comprising:

receiving information about a number of times an endoscope is used; and comparing the number of times used with a predetermined number of times, wherein when the number of times used is equal to or larger than the predetermined number of times, the method:

gives an instruction to overwrite image correction data unique to the endoscope and stored by the endoscope, overwrites the image correction data with new data different from the image correction data in response to the instruction, receives the new data from the endoscope, receives endoscopic image data from the endoscope, and corrects the endoscopic image data using the new data and generates a corrected image.

Example 18. The image generation method according to Example 17, wherein when the number of times used is smaller than the predetermined number of times, the method:

receives the image correction data from the endoscope;

receives endoscopic image data from the endoscope, and corrects the endoscopic image data using the image correction data and thereby generates the corrected image.

Example 19. A storage medium, which is a computer-readable non-transitory storage medium storing a computer program, the computer program causing a computer to:

receive information about a number of times an endoscope is used; and compare the number of times used with a predetermined number of times, wherein when the number of times used is equal to or larger than the predetermined number of times, the computer program further causes the computer to:

give an instruction to overwrite image correction data unique to the endoscope and stored by the endoscope, overwrite the image correction data with new data different from the image correction data in response to the instruction, receive the new data from the endoscope, receive endoscopic image data from the endoscope, and correct the endoscopic image data using the new data and generate a corrected image.

Example 20. The storage medium according to Example 19, wherein when the number of times used is smaller than the predetermined number of times, the computer program causes the computer to:

receive the image correction data from the endoscope;

receive endoscopic image data from the endoscope; and correct the endoscopic image data using the image correction data and generate the corrected image.

Example 21. An endoscope system comprising:

a second processor configured to overwrite an image correction data with a new image correction data when a number of times an endoscope is used is equal to or larger than a predetermined number of times, a video processor configured to:

when the number of times the endoscope is used is smaller than the predetermined number of times, the is configured to:

receive the image correction data, and obtain a first image based on an endoscopic image data by using the new image correction data received, when the number of times the endoscope is used is equal to or larger than the predetermined number of times, receive a new image correction data, and obtain a second image based on the endoscopic image data by using the new image correction data.

Example 21. The endoscope system according to Example 22, further comprising:

an endoscope including a first memory, and wherein the first memory is configured to store one of the image correction data and the new image correction data.

Example 23. The endoscope system according to Example 21, wherein endoscope including a second memory, wherein the second memory is configured to store the number of times the endoscope is used.

Example 24. The endoscope system according to Example 21, further comprising:

an endoscope configured to obtain the endoscopic image data, an adapter connected to the endoscope and the video processor, wherein the adapter includes the second processor.

Example 25. The endoscope system according to Example 24, wherein the first image is a normal image, and wherein the second image is not the normal image.

Example 26. The endoscope system according to Example 25, wherein the second image is obtained to include at least one of below condition:

(i) to includes a normal pixel designated as a defective pixel;

(ii) by shifting a timing to read the endoscopic image data from a normal timing;

(iii) to be smaller or larger than the first image;

(iv) to be varied a white balance from a white balance of the first image; or (v) to be maximized an exposure period to obtain the endoscopic image data.

Example 27. An endoscope system comprising:

a first processor configured to:

receive an information about a number of times an endoscope is used, and determine if the number of times the endoscope is used is equal to or larger than a predetermined number of times, a second processor configured to overwrite an image correction data with a new image correction data when the number of times the endoscope is used is equal to or larger than the predetermined number of times.

Example 28. The endoscope system according to Example 27, further comprising a video processor, wherein the video processor is configured to:

when the number of times the endoscope is used is equal to or larger than the predetermined number of times, receive an image correction data, and obtain a first image based on an endoscopic image data by using the image correction data received, when the number of times the endoscope is used is smaller than the predetermined number of times, the is configured to:

receive a new image correction data, and obtain a second image based on the endoscopic image data by using the new image correction data received, wherein the video processor including one or more of the first processor and the second processor.

Example 29. The endoscope system according to Example 28, wherein the first processor and the second processor are provided integrally.

Example 30. The endoscope system according to Example 27, further comprising an endoscope, wherein the endoscope includes one or more of the first processor the second processor.

Example 31. The endoscope system according to Example 30, wherein the first processor and the second processor are provided integrally.

Example 32. The endoscope system according to Example 27, further comprising:

an endoscope that is configured to obtain the endoscopic image, an adapter connected to the endoscope and the video processor, wherein the adapter including one or more of the first processor and the second processor.

Example 33. The endoscope system according to Example 27, further comprising:

an endoscope that is configured to obtain the endoscopic image, wherein the first processor is configured to:

detect a connection between the endoscope and the video processor, and receives the information about the number of times used.

Example 34. The endoscope system according to Example 27, further comprising a video processor, wherein the video processor is configured to:

when the number of times the endoscope is used is equal to or larger than a predetermined number of times, receive the image correction data, and obtain a first image based on an endoscopic image data by using the new image correction data received, when the number of times the endoscope is used is smaller than the predetermined number of times, receives the new image correction data, and obtain a second image based on the endoscopic image data by using the new image correction data.

Example 35. An image generation method comprising:

receiving information about a number of times an endoscope is used; and determining if the number of times used is equal to or larger than a predetermined number of times, overwriting the image correction data with new image correction data when the number of times used is equal to or larger than the predetermined number of times.

Example 36. The image generation method according to Example 35, wherein when the number of times used is equal to or larger than the predetermined number of times, the method comprising:

receiving the new image correction data from the endoscope, obtaining a second image based on an endoscopic image data by using the new image correction data.

Example 37. The image generation method according to Example 36, wherein when the number of times used is smaller than the predetermined number of times, the method comprising:

receiving the image correction data from the endoscope;

obtaining a first image based on the endoscopic image data by using the image correction data.

Example 38. A storage medium, which is a computer-readable non-transitory storage medium storing a computer program, the computer program causing a computer to:

receive information about a number of times an endoscope is used; and determine if the number of times used is equal to or larger than a predetermined number of times, overwrite the image correction data with new image correction data different from the image correction data in response to the instruction when the number of times used is equal to or larger than the predetermined number of times, the computer program.

Example 39. The storage medium according to Example 38, wherein when the number of times used is equal to or larger than the predetermined number of times, the method comprising:

receive the new image correction data from the endoscope; and obtain a second image based on an endoscopic image data by using the new image correction data.

Example 40. The storage medium according to Example 39, wherein when the number of times used is smaller than the predetermined number of times, the computer program causes the computer to:

receive the image correction data from the endoscope; and obtain a first image based on the endoscopic image data by using the image correction data.

What is claimed is:

1. A control device for use with an endoscope, comprising:

at least one processor configured to:

receive an information including a number of times the endoscope is used;

determine if the number of times the endoscope is used is smaller than or equal to or larger than a predetermined number of times;

in response to determining the number of times the endoscope is used is smaller than the predetermined number of times, generate a first image; and in response to determining the number of times the endoscope is used is equal to or larger than the predetermined number of times, generate a second image, wherein a first visibility of the first image is higher than a second visibility of the second image, wherein the first visibility and the second visibility depend on a timing to read endoscopic image data from the endoscope.

2. The control device according to claim 1, wherein in response to determining the number of times the endoscope is used is equal to or larger than the predetermined number of times, the at least one processor is configured to overwrite a first image correction data with a second image correction data, wherein the first image is generated based on an image signal and the first image correction data, and wherein the second image is generated based on the second image correction data.

3. The control device according to claim 2, wherein the at least one processor comprises a first processor and a second processor, wherein the first processor is configured to receive the information including the number of times the endoscope is used and determine if the number of times the endoscope is used is equal to or larger than the predetermined number of times, wherein the second processor is configured to overwrite the first image correction data with the second image correction data, and wherein the control device further comprises a video processor.

4. The control device according to claim 3, wherein the endoscope further includes a first memory, and wherein the first memory is configured to store one of the first image correction data and the second image correction data.

5. The control device according to claim 4, wherein the endoscope further includes a second memory, and wherein the second memory is configured to store the information including the number of times the endoscope is used.

6. The control device according to claim 5, wherein the at least one processor is further configured to:

detect a connection between the endoscope and the video processor, and receive the information including the number of times the endoscope is used from the second memory.

7. The control device according to claim 2, further comprising an adapter connected to the endoscope and the at least one processor, wherein the at least one processor includes a first processor and a second processor, wherein the first processor is configured to receive the information including the number of times the endoscope is used and determine if the number of times the endoscope is used is equal to or larger than the predetermined number of times, wherein the second processor is configured to overwrite the first image correction data with the second image correction data, and wherein the adapter includes the second processor.

8. The control device according to claim 1, further comprising a video processor, wherein the video processor includes the at least one processor.

9. The control device according to claim 1, wherein, when the first visibility of the first image is higher than the second visibility of the second image, the at least one processor is configured to at least one of:

(i) obtain the second image including a number of a defective pixel that is higher than a number of a defective pixel included in the first image;

(ii) shift a timing to read endoscopic image data from a timing to read endoscopic image data to obtain the first image;

(iii) obtain the second image to be smaller or larger than the first image;

(iv) obtain the second image including a white balance different from a white balance of the first image;

(v) obtain the second image by using endoscopic image data obtained by a maximum exposure period, (vi) obtain the second image having a different size from the first image; or (vii) obtain the second image having a different exposure from the first image.

10. The control device according to claim 1, wherein the at least one processor is configured to obtain the second image including a number of a defective pixel that is higher than a number of a defective pixel included in the first image.

11. The control device according to claim 1, wherein the at least one processor is configured to output one of the first image or the second image to a display that is different from the endoscope.

12. The control device according to claim 1, wherein the at least one processor is configured to:

determine whether to finish processing; and in response to determining the number of times the endoscope is used is equal to or larger than the predetermined number of times, and in response to determining the processing is finished, overwrite a first image correction data with a second image correction data.

13. The control device according to claim 12, wherein the at least one processor is configured to generate one of the first image or the second image in response to determining the processing is not finished.

14. An image generation method, comprising:

receiving information including a number of times an endoscope is used;

determining if the number of times the endoscope is used is smaller than or equal to or larger than a predetermined number of times;

in response to determining the number of times the endoscope is used is smaller than the predetermined number of times, generating a first image; and in response to determining the number of times the endoscope is used is equal to or larger than the predetermined number of times, generating a second image, wherein a first visibility of the first image is higher than a second visibility of the second image, wherein the first visibility and the second visibility depend on a timing to read endoscopic image data from the endoscope.

15. The image generation method according to claim 14, wherein, in response to determining the number of times the endoscope is used is equal to or larger than the predetermined number of times, the method further comprises:

overwriting a first image correction data with a second image correction data, wherein the first image is generated based on an image signal and the first image correction data.

16. The image generation method according to claim 15, wherein the second image is generated based on the second image correction data.

17. The image generation method according to claim 14, further comprising:

outputting one of the first image or the second image to a display that is different from the endoscope.

18. A non-transitory computer-readable medium having instructions stored thereon, which when implemented by a processor causes the processor to execute a method, the method comprising:

receiving information including a number of times an endoscope is used;

comparing the number of times the endoscope is used to a predetermined number of times; and in response to determining the number of times the endoscope is used is smaller than the predetermined number of times, generating a first image, in response to determining the number of times the endoscope is used is equal to or larger than the predetermined number of times, generating a second image, wherein a first visibility of the first image is higher than a second visibility of the second image, wherein the first visibility and the second visibility depend on a timing to read endoscopic image data from the endoscope.

19. The non-transitory computer-readable medium according to claim 18, wherein, in response to determining the number of times the endoscope is used is equal to or larger than the predetermined number of times, the method further includes:

overwriting a first image correction data with a second image correction data, and wherein the first image is generated based on an image signal and the first image correction data.

20. The non-transitory computer-readable medium according to claim 18, wherein the method further comprises:

outputting one of the first image or the second image to a display that is different from the endoscope.

* * * * *